United States Patent [19]
Scarffe

[11] Patent Number: 5,841,027
[45] Date of Patent: Nov. 24, 1998

[54] PIEZOELECTRIC FLOW TRANSDUCER

[75] Inventor: Michael F. Scarffe, Little Horwood, United Kingdom

[73] Assignee: AZTEC Development Ltd, United Kingdom

[21] Appl. No.: 936,668

[22] Filed: Sep. 24, 1997

Related U.S. Application Data

[62] Division of Ser. No. 381,909, filed as PCT/GB93/01579, Jul. 27, 1993, Pat. No. 5,716,038.

[30]     Foreign Application Priority Data

Aug. 13, 1992 [GB] United Kingdom .................. 9217180

[51] Int. Cl.$^6$ ..................................................... G01F 15/02
[52] U.S. Cl. ................................................................ 73/198
[58] Field of Search ..................................... 310/332, 334; 73/861, 195, 197, 198

[56]            References Cited

U.S. PATENT DOCUMENTS

| | | |
|---|---|---|
| 3,365,593 | 1/1968 | Roof . |
| 3,797,526 | 3/1974 | Champeon . |
| 3,980,002 | 9/1976 | Jarmon . |
| 4,140,012 | 2/1979 | Hendriks . |
| 4,144,752 | 3/1979 | Lolk . |
| 4,248,270 | 2/1981 | Ostrowski . |
| 4,325,262 | 4/1982 | Meisser . |
| 4,469,976 | 9/1984 | Scott . |
| 4,487,333 | 12/1984 | Pounder . |
| 4,500,002 | 2/1985 | Zukausky . |
| 4,500,067 | 2/1985 | Zukausky . |
| 4,558,249 | 12/1985 | Lerch et al. . |
| 4,577,132 | 3/1986 | Ohigashi . |
| 4,728,844 | 3/1988 | Wilson . |
| 4,955,507 | 9/1990 | Kirschner . |
| 5,033,644 | 7/1991 | Tentler . |
| 5,048,790 | 9/1991 | Wells . |
| 5,082,240 | 1/1992 | Richmond . |

FOREIGN PATENT DOCUMENTS

| | | |
|---|---|---|
| 0 356 057 | 2/1990 | European Pat. Off. . |
| 1 263 425 | 3/1968 | Germany . |
| 1 116 474 | 6/1968 | United Kingdom . |
| 1 127 081 | 9/1968 | United Kingdom . |
| 1 203 638 | 8/1970 | United Kingdom . |
| 2 259 156 | 3/1993 | United Kingdom . |
| 8 401 806 | 5/1984 | WIPO . |

OTHER PUBLICATIONS

Lewin, et al: "Wide-band piezoelectric polymer acoustiv source", IEEE Transactions on Ultrasonics, Ferroelectrics and Frequency Control, vol. 35, No. 2, Mar. 1988, pp. 175–184.

*Primary Examiner*—William L. Oen
*Attorney, Agent, or Firm*—Cushman Darby & Cushman Intellectual Property Group of Pillsbury Madison & Sutro, LLP

[57]             ABSTRACT

A system for dispensing mixed beverages has a processor to control the liquid dispensed at an outlet in dependence upon the demand of a user as input to a keypad. Carbonated water is fed to the outlet by way of tubing and a syrup concentrate is also fed therto by way of a tubing. The water and syrup is mixed in the correct quantities by way of respective proportional valves which adjust the quantity or flow rate of the two consituents fed through a mixing chamber in accordance with flow rate readings provided to the processor by respective flow transducers. The flow transducers measure the speed of flow ultrasonically and are able to provide flow rate readings at a rate of 50 per second. The proportional valves are able to adjust the quantities fed to the mixing chamber at a similar rate such that the mix can be reliably determined even if there are transitory pressure drops or viscosity changes in the system.

13 Claims, 4 Drawing Sheets

PIEZOELECTRIC FLOW TRANSDUCER

This is a division of application Ser. No. 08/381,909, filed as PCT/GB93/01579 Jul. 27, 1993, now U.S. Pat. No. 5,716,038.

The present invention relates to a method and system for dispensing fluids, and to a sensor, transducer and proportional valve for use in such a system or with such a method.

To avoid the need to transport and store water, it is becoming common to dispense beverages, for example, by mixing a concentrate with water at the point of sale. However, the resultant beverages dispensed by the systems which are currently available are generally variable in quality. For example, if water and concentrate are dispensed from individual pipes, but at more than one location, the resultant pressure drops and viscosity variations change the water to concentrate volumetric ratio of the beverage being dispensed. In this respect, currently available mechanical means for controlling the flow of a liquid during a dispense cannot be made to react to changes in the pressure drop, viscosity or flow rate of the liquids.

It is an object of the present invention to provide a method and system for reliably dispensing fluids, which method and system reduces the disadvantages of the known systems. The invention also seeks to provide component parts for such a system.

According to a first aspect of the present invention, there is provided a piezoelectric sensor for a sonic transducer, said sensor comprising a housing defining an opening, a piezoelectric element comprising a piezoelectric film mounted to extend across said opening, electrically conductive regions contacting opposed surfaces of said piezoelectric film and overlying to define one area of said piezoelectric film at which the opposed conductive regions coincide, and means for making electrical connections to said conductive regions, wherein said means for making electrical connections comprises an electrically conductive post extending within said housing, an end surface of said post contacting one surface of said piezoelectric film at said one area thereof.

When electrical signals, for example, electrical pulses, are applied to said electrically conductive regions, it is only at said one area of the piezoelectric film that the pulse is applied across the thickness of the piezoelectric film. Accordingly, it is only at said one area that mechanical deformation takes place. A sensor of the invention is thereby able to output a sound wave from said one area only. Preferably, the sensor of the invention is arranged to output an ultrasonic waveform.

The electrically conductive post which is arranged to contact said one surface of said piezoelectric film acts to maximise the ultrasonic waves emitted.

The electrically conductive regions may be defined, for example, by electrically conductive films provided on opposing surfaces of said piezoelectric film. In this case, said end surface of said electrically conductive post contacts the electrically conductive film provided on said one surface of the piezoelectric film.

However, it is presently preferred that the end surface of said post directly contacts said one surface of the piezoelectric film and thus defines one of said electrically conductive regions. In this case, it is also presently preferred that said other electrically conductive region is defined by an electrically conductive film provided on the other surface of the piezoelectric film.

Any suitable piezoelectric film may be utilized.

In a preferred embodiment of the invention, it is preferred that the piezoelectric film be a film of polyvinylidene fluoride (PVDF).

In a preferred embodiment the electrically conductive film is preferably a film of gold. Not only is gold conductive, it is also inert, and this latter property is clearly important if the sensor is to be used, for example, in a transducer to measure the properties of a beverage.

In an embodiment, the electrically conductive film is applied to the or each surface of the piezoelectric film by vapour deposition.

If electrically conductive film is applied to both surfaces of the piezoelectric film, one surface of the piezoelectric film may be entirely covered with the electrically conductive film except for a single cutout, whilst the other surface may have a small area only of electrically conductive film, at least part of which does not coincide with the cutout. Said at least part of the small area of the electrically conductive film on the other surface will thereby define with the electrically conductive film on the first surface thereof said one area of the piezoelectric element.

Preferably, said one area of the piezoelectric film is substantially circular. It is also preferred that said circular area is located substantially centrally of the piezoelectric film.

In a preferred embodiment, the piezoelectric film is generally circular.

The means for making electrical connections to said electrically conductive regions preferably comprises at least the opening of said housing, said opening being arranged to surround and contact the periphery of one of the surfaces of the piezoelectric film. Said conductive post extends substantially transversely with respect to the piezoelectric film.

Preferably, said piezoelectric element is supported on a plastics material body which is received within said housing.

The plastics material body is preferably substantially cylindrical and may be provided with an axial bore therethrough in which said conductive post extends, said bore extending substantially centrally of the plastics body. Electrical connections may be made directly to said conductive post or by way of an electrical terminal also extending within said plastics body.

Although it is possible to form a plastics material body and subsequently to insert appropriate posts and terminals therein, it is presently preferred that said plastics material body has been formed by being moulded around said conductive post.

The invention also extends to a method of forming a piezoelectric sensor, the method comprising the steps of moulding a plastics material body around a conductive post, machining one surface of said body and post, affixing a piezoelectric film onto said machined surface such that a machined end of said post is electrically connected to one surface of said piezoelectric film, providing an electrically conductive region on the other surface of said piezoelectric film, and mounting the body, post and film in a housing.

According to a further aspect of the present invention there is provided a flow transducer for measuring the flow rate of a fluid, said flow transducer comprising an elongate measuring chamber along which a fluid is arranged to flow, an upstream sensor at an upstream end of said measuring chamber, and a downstream sensor at a downstream end of said measuring chamber, wherein each said sensor is controllable to emit and/or receive a sound beam and is arranged such that sound beams emitted pass along said measuring chamber, and wherein said measuring chamber is substantially linear, and is arranged to diverge in the direction of fluid flow.

Preferably, a section of said measuring chamber at the upstream end thereof is tapered inwardly in the direction of fluid flow. This avoids the formation of a vena contractor.

The invention also extends to a flow transducer for measuring the flow rate of a fluid, said flow transducer comprising an elongate measuring chamber along which a fluid is arranged to flow, an upstream sensor at an upstream end of said measuring chamber, and a downstream sensor at a downstream end of said measuring chamber, wherein each said sensor is controllable to emit and/or receive a sound beam and is arranged such that sound beams emitted pass along said measuring chamber, and wherein a section of said measuring chamber at the upstream end thereof is tapered inwardly in the direction of fluid flow.

The flow transducer may be used to measure the flow rate of any fluid, but is preferably used for measuring the flow rate of liquids to be dispensed.

According to a still further aspect of the present invention there is provided a flow transducer comprising a measuring chamber for the fluid, at least one sensor controllable to emit a sound beam into the fluid, and temperature determining means for determining the temperature of the fluid in the measuring chamber.

Preferably, said measuring chamber is elongate and the fluid is arranged to flow therealong, and an upstream sensor is arranged at a upstream end of said measuring chamber, and a downstream sensor is arranged at a downstream end of said measuring chamber.

Preferably, the measuring chamber diverges in the direction of fluid flow such that the included angle does not exceed 2°. Preferably the included angle of the diverging measuring chamber is in the range of 0.5° to 1°. In a preferred embodiment, the included angle in 0.67°.

Preferably, said upstream and downstream sensors are arranged such that sound beams emitted thereby are substantially aligned and pass along a central longitudinal axis of said measuring chamber.

In an embodiment, the flow transducer has a fluid inlet communicating with the measuring chamber to supply fluid thereto, and a fluid outlet communicating with the measuring chamber to receive fluid therefrom. Preferably, a tortuous path for the fluid is defined between the fluid inlet and the measuring chamber, and between the measuring chamber and fluid outlet, the arrangement being such that fluid is constrained to flow substantially symmetrically across a transmitting face of both the upstream and the downstream sensors.

In an embodiment, the longitudinal axes of the fluid inlet and of the fluid outlet are aligned, and this common longitudinal axis is spaced transversely from the central longitudinal axis of the measuring chamber.

In an alternative embodiment, the longitudinal axis of one of the fluid inlet and the fluid outlet extends substantially perpendicularly with respect to the central longitudinal axis of the measuring chamber, whilst the longitudinal axis of the other of the fluid outlet and the fluid inlet extends substantially parallel to, but spaced transversely from, the central longitudinal axis of the measuring chamber.

In a preferred embodiment, each said sensor comprises a piezoelectric element arranged, upon the application of electrical signals thereto, to emit an ultrasonic pulse or pulses. The piezoelectric element of each sensor is also able to receive an ultrasonic sound wave and output a responsive electrical signal.

In a preferred embodiment, each of the sensors of the flow transducer comprises a sensor as defined above.

Traditionally, sensors incorporating piezoelectric elements utilize such elements made of a ceramic. However, a ceramic has a poor acoustic impedance match with water, because the density of a ceramic is very much higher than that of water. Ceramics also have bell like qualities in that the vibrations induced therein persist. Accordingly, in a preferred embodiment of the invention, the piezoelectric element of each sensor is formed by a PVDF film. Such a film has a density close to that of water, for example the density is generally of the order of 1.3 gms\cc. This means that low energy is required to input the signal into the liquid, and that there is a fast rise time, that is, the response is good.

According to a further aspect of the present invention there is provided a flow control valve for controlling the flow of a fluid, said flow control valve having a fluid inlet, a fluid outlet, a main valve member controlling communication between said inlet and said outlet, means for biassing said main valve member into a closed position in which communication between said inlet and said outlet is closed, and means for moving said main valve member against the action of said biassing means to open the valve, the flow control valve further comprising a pilot chamber which is in communication with said fluid inlet, pressure within said pilot chamber being applied to said main valve member in a direction to oppose opening of said valve, and wherein said main valve member is arranged to define a flow path with said outlet, the area of which flow path varies in dependence upon the position of said valve member and increases as the valve member is moved in the valve opening direction, and wherein the position of the valve member and hence the rate of flow of fluid through the valve is determined by said moving means.

The flow control valve may be used for controlling the flow of any fluid, but can particularly be used for controlling the flow of liquids to be dispensed.

In a preferred embodiment, said means for moving the valve member comprises a magnetic armature arranged to be moved by the application of electrical current to a magnetic circuit. In this respect, the amount of movement of the armature is arranged to be substantially directly proportional to the amplitude of the applied electrical current.

Preferably, the fluid outlet is defined at one end of a tubular member whose other end defines a main valve seat, the main valve member being arranged to abut said valve seat in its closed position, and the main valve member having a converging portion extending within said tubular member. Movement of the main valve member away from the main valve seat is arranged to move the converging portion of the valve member along the tubular member and hence to vary the area of the flow path.

Preferably, means are provided to constrain said converging portion of the main valve member to only move longitudinally within said tubular member. For example, said constraining means may comprise at least three longitudinally extending vanes, or other projecting means, arranged to contact the inner surface of said tubular member.

Preferably, the pilot chamber is defined by a diaphragm carried by said main valve member, and at least one aperture is provided in said diaphragm to communicate the pilot chamber and the fluid inlet.

A pilot valve to enable initial opening of the valve and to ensure that the main valve member follows the movement of the armature is provided in the pilot chamber. The pilot valve comprises a pilot valve pad carried by the free end of said armature, said pilot valve pad being arranged to seat on said main valve member to close a pilot bore extending therethrough.

The present invention also extends to a method for dispensing fluids, the method comprising the steps of flowing a fluid to be dispensed to a dispensing outlet, sensing the rate of flow of the fluid, and continually controlling the quantity and/or the flow rate of the fluid dispensed by way of said dispensing outlet in dependence upon said sensed flow rate.

According to a further aspect of the present invention there is provided a method of dispensing fluids, the method comprising the steps of flowing a fluid to be dispensed to a dispensing outlet, sensing or determining at least one physical parameter of the fluid, comparing the parameter(s) sensed or determined with predetermined values, and, if the sensed and determined parameter(s) are outside said predetermined values, locking said dispensing outlet to prevent the dispensing of fluid thereby.

The method according to this aspect of the invention enables a dispensing operation to be halted where imitation or substitute fluids are detected by differences in their physical parameters.

The present invention also extends to a method of testing a fluid, the method comprising the steps of storing data representative of the speed of sound in a genuine fluid at various temperatures, testing a fluid to determine information representative of the speed of sound in the tested fluid, and determining information representative of the temperature of the tested fluid, and determining if the tested fluid is genuine by comparing the determined information with the stored data.

In a preferred embodiment, the method further comprises continually adjusting the sensed flow rate of the fluid such that the fluid is dispensed by way of said dispensing outlet at a selected flow rate and/or in a selected quantity.

Dispensing the fluid in dependence upon the sensed flow rate, as in a method of the invention, enables, for example, a selected quantity, to be reliably dispensed even if the pressure or flow rate of the fluid falls. This may occur, for example, where the fluid is being simultaneously dispensed from a number of outlets.

In an embodiment, a method of the invention may comprise flowing a fluid selectively to a plurality of dispensing outlets, and controlling the quantity and/or the flow rate of the fluid dispensed by way of each said dispensing outlet in dependence upon said sensed flow rate.

In a practical environment, it would generally be carbonated water and concentrates which are required to be flowed from tubing therefor to selected ones of a number of dispensing outlets.

A method of the invention has particular utility for dispensing post-mix liquids, for example, beverages mixed at the dispensing outlet from more than one liquid.

In a post-mix embodiment of the invention, the method further comprises flowing a second liquid to be dispensed to said dispensing outlet, sensing the flow rate of the second liquid to the dispensing outlet, and continually controlling the quantity and/or the flow rate of each liquid dispensed from said dispensing outlet in dependence upon its sensed flow rate.

The invention also extends to a method of dispensing mixed fluids, the method comprising the steps of flowing first and second fluids to be mixed and dispensed to a dispensing outlet, sensing the rate of flow of each of said first and second fluids, and continually controlling the quantity and/or flow rate of each fluid dispensed from said dispensing outlet in dependence upon its sensed flow rate.

In an embodiment, the method further comprises the step of adjusting the sensed flow rate of one or each of said first and second fluids such that the mixed fluid dispensed by said dispensing outlet contains the first and second fluids in selected relative proportions.

Preferably, the first and second fluids are two liquids to be mixed to dispense a beverage. For example, the liquids may be water and a concentrate.

As a method of the invention dispenses two liquids at a quantity or rate dependant upon their sensed flow rates, it enables a mix to be dispensed at a dispensing outlet in which the two liquids are in a predetermined proportion or ratio.

It may be that the selected relative proportions are required to differ, for example, because different liquids are being dispensed and/or for taste reasons. A method of the invention can be arranged to vary the relative proportions selected.

In a preferred embodiment of the methods defined above, information as to the selected rate, and/or selected quantity, and/or selected proportions is supplied to control means, and the sensed flow rate(s) are adjusted by said control means in response to the information.

Preferably, the methods defined above comprise the step of controlling the quantity and/or rate(s) of the liquid(s) dispensed by way of valve means at said dispensing outlet. Generally, the valve means are arranged to be actuated by said control means. For example, where the valve means comprises one or more proportional valves, each said proportional valve is actuated by said control means to dispense liquid at a rate determined by said control means. The control means varies the rate of liquid dispensing by the proportional valve as the sensed flow rate varies.

In embodiments of the methods defined above, the rate(s) of flow may be sensed in any suitable manner. Preferably, the sensing of the rate(s) of flow is performed ultrasonically.

According to a further aspect of the present invention, there is provided a system for dispensing fluids, said system comprising at least one dispensing outlet, tubing for flowing a fluid to said dispensing outlet, sensing means for sensing the rate of flow of said fluid through said tubing, and flow control means responsive to the sensing means and arranged to continually control the quantity and/or rate of fluid dispensed through said dispensing outlet in dependence upon the sensed flow rate.

The invention also extends to a system for testing a fluid comprising processor means for storing data representative of the speed of sound in a genuine fluid at various temperatures, first determining means for determining information representative of the speed of sound in a tested fluid, and second determining means for determining information representative of the temperature of the tested fluid, said processor means being arranged to receive said determined information from said first and second determining means and to compare said determined information with said stored data.

The dispensing system may include means to lock the dispensing outlet where imitation or substitute fluids are detected, for example, by the testing system defined above.

Preferably, said flow control means comprises valve means for controlling the flow of fluid through said dispensing outlet, and control means responsive to said sensing means and arranged to actuate said valve means.

In a preferred embodiment, said valve means comprises at least one proportional valve actuable to vary the flow rate of fluid through said dispensing outlet.

Where it is required to dispense mixed liquids, particularly where the liquids in the mixture are to be dispensed in selected relative proportions, a respective proportional valve may be provided to control the flow of each liquid. Preferably, said dispensing outlet is provided at the outlet of a mixing chamber into which each said proportional valve dispenses.

In a preferred embodiment, the or each said proportional valve is as defined more particularly above.

Said control means is preferably arranged to actuate valve means controlling the flow of a plurality of fluids. In this case, sensing means for sensing the rate of flow of each said fluid are preferably provided, and said control means is responsive to each sensed rate of flow.

In a preferred embodiment, said control means comprises processor means having an associated memory. Information as to required flow rate(s), required quantity, and/or required proportions of fluids to be dispensed is preferably stored in said memory, and said processor means is arranged to control said valve means in dependence upon the information stored in memory and the sensed flow rates.

Preferably, said processor means is also arranged to be responsive to user demands and requirements. For example, the processor means is coupled to input means arranged to supply demand information. Preferably, said input means comprises a keypad.

In an embodiment, there is a two-way communication between the processor means and the input means.

Said sensing means preferably comprises a respective flow transducer for the or each fluid to be dispensed. Preferably, each flow transducer is arranged in tubing for flowing the associated fluid to a dispensing outlet, and preferably, each said flow transducer is in two-way communication with said processor means.

In a preferred embodiment, each said flow transducer is arranged to sense the flow rate ultrasonically. The processor means is arranged to control the ultrasonic sensing process and to compute the flow rate from data provided by the transducer.

In a preferred embodiment, the or each flow transducer is as defined more particularly above.

Embodiments of the present invention will hereinafter be described, by way of example, with reference to the accompanying drawings, in which.

Figure 1:
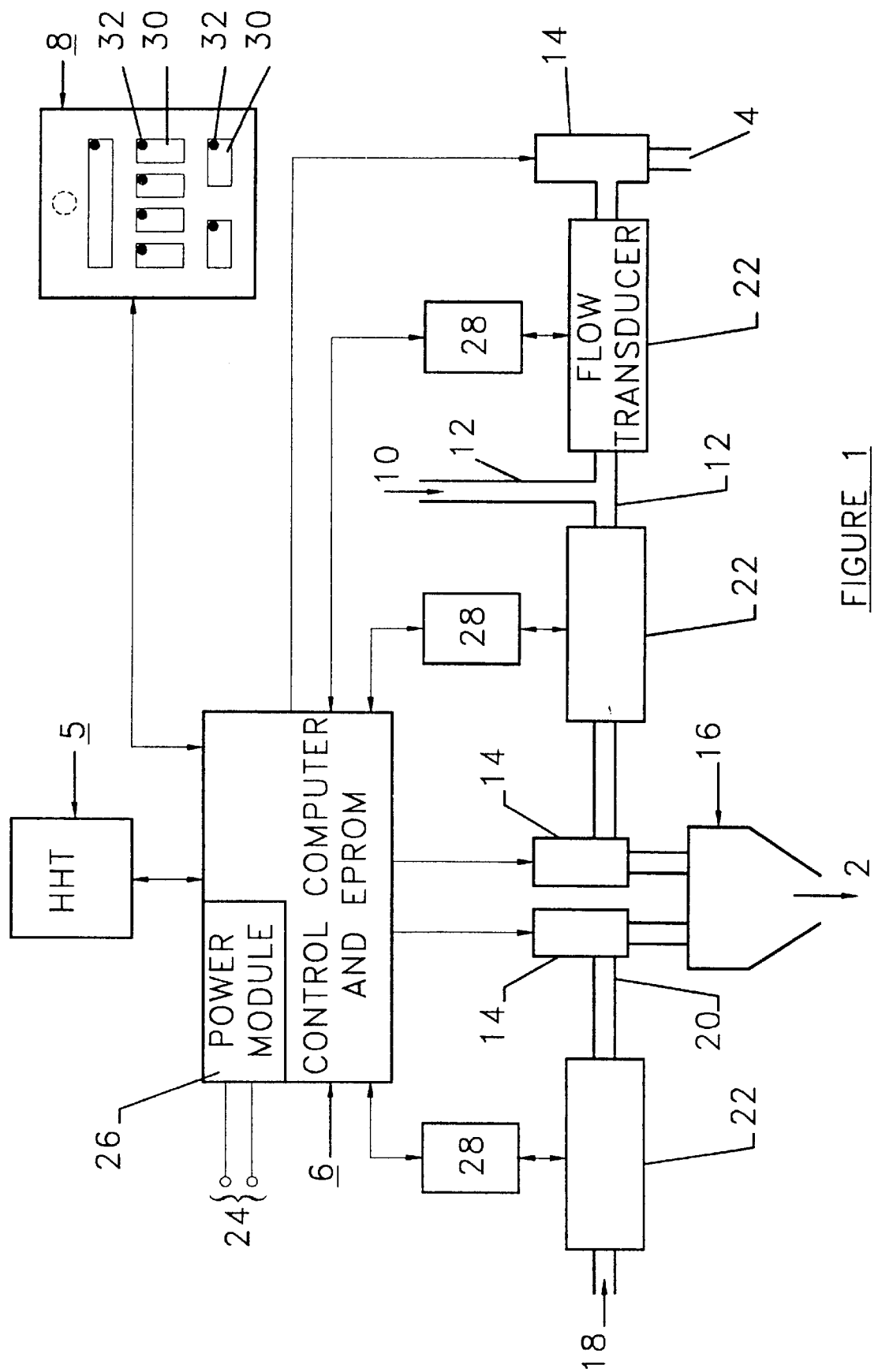
FIG. 1 shows a block diagram of a system for dispensing liquids.

The drawings illustrate one embodiment of a post-mix dispensing system for beverages. Increasingly, beverages, for example, colas and fruit drinks, are mixed at the point of sale. In this respect a syrup concentrate is mixed as it is dispensed with carbonated water. Post-mixing has the advantage over pre-mixed beverages that there is no longer any need to transport the water which makes up the majority of the volume of the beverage, or the containers, which are conventionally glass bottles or cans, and therefore there are considerable savings in transportation costs. It is also easier to store concentrates than pre-mixed and packaged beverages, and stock control is also simpler. However, in order to dispense the required beverage, it is extremely important that the concentrate and the carbonated water are mixed in the appropriate proportions. Most concentrates are provided by their manufacturers, for example, in a concentration requiring that the final beverage be made from five parts carbonated water to one part concentrate by volume.

In public houses and other venues where beverages are dispensed, it is now common to provide a facility to pipe carbonated water and concentrates to one or more dispensing stations which also include mechanical dispensers for at least one concentrate. The dispensing station is arranged to dispense both the concentrate and the water to provide a mixed beverage, and the dispensing station tries to keep the flow therethrough relatively constant so that the mixed beverage dispensed has the appropriate relative proportions. However, the known devices cannot guarantee that the mixed beverage dispensed reliably has its constituents in the required proportions. In this respect, the dispensing station will generally be arranged such that the carbonated water is dispensed contemporaneously with the concentrate but at a flow rate which is five times that of the concentrate. However, the tubing carrying the carbonated water and that carrying the concentrates is generally of a considerable length so that there is a pressure drop therealong which affects the flow rate therethrough. Traditionally more than one dispensing station is fed by each carbonated and concentrate supply and the pressure drop at a dispensing station will also vary depending upon whether more than one dispensing station is dispensing at the same time. The existing mechanical systems, therefore, cannot reliably dispense mixed beverages. Furthermore, the mechanical systems cannot provide a mix of different proportions for different concentrates at the same dispensing station.

Dispensing of the fluids is by way of valves which are turned on and off as required. For example, electrically actuable solenoid valves may be provided, and there have been proposals to improve the reliability of the mix by measuring the fluid flow rates and timing the actuation of the valves in dependence thereon.

However, such digital systems are not sufficiently responsive and are simply not able to react at the speeds necessary to cope with transients and thus to provide the reliability required.

A dispensing system as described and illustrated in the accompanying drawings is able to reliably dispense mixed beverages at the proportions required. It is also able to dispense different concentrates in different proportions, and its reliability is not altered if more than one dispensing station is operated simultaneously. Furthermore, the rate of flow of the beverage can be controlled in dependence upon the portion to be dispensed. This is useful, for example, if it is required to dispense a small portion. It is also helpful if a quantity of a beverage is dispensed initially at a slow rate and subsequently at a faster rate, as this prevents splashing and foaming. Again, this is a feature of a dispensing system of the invention.

The reliability of the dispensing achieved by the system described and illustrated herein arises out of its ability to respond substantially immediately to changes in the system. This means that the system can cope with transients.

The embodiment described and illustrated below is a dispensing system for dispensing mixed beverages such as cola and fruit drinks made from a mixture of syrup concentrate and carbonated water. However, it will be appreciated that the invention is not limited to the particular liquids or beverages which are being dispensed and that the system may be used for any dispensing operation required. For example, where a number of dispensing outlets connected to a common supply tubing are required, a dispensing system of the invention can be utilized to ensure that fluids can be dispensed from one or more of the outlets at similar rates, rather than one outlet being favoured, as occurs in present systems. Additionally and/or alternatively, the system may be used to dispense any mixed fluid where it is wished to reliably control the relative proportions of the fluids in the mix.

It will be appreciated that different fluids have different physical characteristics. Proprietary colas, for example, are either imitated or diluted with water and the imitations have physical characteristics which differ from those of the proprietary brands. A system of the invention can be arranged to detect such variations and this can be used to control or prevent fraudulent dilution or substitution of imitations. Thus, additionally and/or alternatively a dispensing system of the invention can be used for any dispensing operation where it is wished to prevent or detect the dispensing of substitute fluids.

For clarity, the description of the embodiments given below refers specifically to the dispensing of mixed beverages made from syrup concentrate and carbonated water.

FIG. 1 shows a block diagram of a system of the invention for dispensing beverages. In the embodiment illustrated in FIG. 1 there are provided two dispensing outlets 2,4, the first outlet 2 being arranged to dispense a mixed beverage, and the second outlet 4 being arranged to dispense carbonated water only. The beverages are dispensed upon the demand of a user which is input to the system by way of a keypad 8. The keypad 8 is in two-way communication with a processor 6 which controls the dispensing of the liquid at the outlets 2,4. It will be appreciated that the processor 6 may be arranged to access and control many more dispensing outlets than the two which are illustrated.

In the illustrated embodiment, carbonated water, indicated by the arrow 10, is arranged to be supplied under pressure to tubing 12. The tubing 12 is tapped at a first point so that water may be fed by way of an outlet valve 14 to the dispensing outlet 4. The tubing is tapped at a second point so that carbonated water may be fed by way of a further outlet valve 14, and a mixing chamber 16, to the dispensing outlet 2. A syrup concentrate, indicated by the arrow 18, is arranged to be supplied by tubing 20 and a further outlet valve 14 to the mixing chamber 16. In this way, the beverage dispensed at the outlet 2 can be a mixture of the concentrate 18 and of the carbonated water 10.

To ensure that the mixture dispensed at the outlet 2 contains the concentrate and the water in predetermined relative proportions, the valves 14 for dispensing the concentrate and water are all proportional valves and are each controlled by the processor 6. In this respect, the processor 6 receives information from respective flow transducers 22 as to the flow rate of the two liquids 10,18, and is arranged to control the valves 14 accordingly so that each proportional valve 14 dispenses a required flow of liquid so as to keep the dispensed mixture reliably in the required proportions.

The processor 6 may be configured by any suitable means. In an embodiment, the processor 6 is a microprocessor provided with memory, for example an EPROM. The processor 6 is arranged to be connected to the mains, as indicated at 24, and a power module 26 for receiving mains power and powering the processor 6 is provided.

As is indicated in FIG. 1, the processor 6 is also connectible to an hand held terminal (HHT) 5. In this respect, the processor 6 is preferably provided with one or more communication ports (not visible) to which any required modules, such as the HHT, are selectively, and releasably, pluggable to communicate with the processor 6.

It is particularly useful to provide for communication between the processor 6 and the HHT 5 as such a link can be used to set up the system initially. Thus, all the necessary initial values, appropriate data, and programs can be set up in the factory and downloaded into the processor 6. This data may be altered on site utilising the HHT 5 if required.

It is, of course, useful to have the ability to communicate with the processor 6, and such an ability can be used for a wide variety of applications. For example, means can be provided to link the processor 6 with Electronic Point of Sale (EPOS) terminals (not shown) to facilitate reconciliation between sales made and fluids dispensed and/or to provide other control and management information. In such a context, the link between processor 6 and EPOS terminal may be made intelligent.

The memory of the processor 6 is arranged to store information as to the required flow rate of the liquids controlled by each valve 14. In this respect, where a syrup concentrate is to be mixed with carbonated water, it is generally required that the liquids be combined in the ratio of 1:5 (concentrate to water). Whilst this dilution is common in the beverage industry, some concentrates are very difficult to flow at that concentration. The system enables such concentrates to be provided in a dilute, more flowable, form and for the processor 6 to control the mixing of such diluted concentrates in different proportions. In fact, the processor 6 may store a different desired ratio for the mix of each concentrate which is to be dispensed.

The flow transducers 22 are described in more detail below. Each transducer 22 is arranged to measure the flow rate of the liquid in the associated tubing 12,20 and to provide flow rate readings to the processor 6. It is those values which the processor 6 utilizes to control the appropriate proportional valves 14. The construction of the proportional valves 14 is also described in greater detail below. In a preferred embodiment, each flow transducer 22 is arranged to provide flow readings for the liquid in the respective tubing fifty times per second.

In the embodiment illustrated, each flow transducer 22 measures the speed of flow ultrasonically. This requires that ultrasound pulses are generated and are transmitted into the flowing liquid. A transducer circuit 28 is associated with each transducer 22 and is arranged to generate the ultrasound pulses and to make timing measurements therefrom. This data is then fed by way of the transducer circuit 28 to the processor 6 so that the processor can determine the flow rate.

Each transducer circuit 28 is associated with, and dedicated to, the operation of a single transducer 22 whereas the processor 6 receives information from all of the transducers 22. In the embodiment illustrated each transducer circuit 28 is arranged to feed raw data to the processor 6. However, it will be appreciated that the functions to be undertaken by the dedicated circuitry 28 and those to be undertaken by the processor 6 can be chosen as required, and depend only upon the capabilities given to the transducer circuit 28. There may be savings in processor time, for example, if, as well as the operational functions, the dedicated transducer circuit 28 undertakes some of the computing of the raw data produced.

It is possible to provide a central input means, such as the keypad 8, for enabling the control of a number of dispensing outlets. Of course, an operator will require that the keypad be proximate to the dispensing outlet being controlled. A single keypad 8 can therefore be provided where a number of dispensing outlets are physically grouped together. However, if it is required to space the dispensing outlets at a number of locations, a number of separate keypads 8, each communicating with the processor 6 may be provided, each keypad 8 providing the ability to cause liquid to be dispensed from an associated dispensing outlet.

The keypad 8 has a number of keys 30, preferably in the form of membrane switches, and enables the operator to demand a quantity of a liquid to be dispensed from an associated outlet, as 2,4. Generally the Trade Mark, or logo, or other identification of the drinks to be dispensed is marked near the keys 30 for simplicity. The operator then only has to press the appropriate key 30 for the required beverage to be dispensed.

It is possible to arrange that actuation of a specific key 30 causes a predetermined quantity of the liquid to be dispensed. However, additionally and/or alternatively, it is possible to require that liquid is dispensed only whilst the appropriate key 30 remains depressed.

Where a key 30 of the keypad 8 is marked with the identification of a particular beverage, for example "Pepsi" or "Orange", it is generally arranged that actuating that key alone will cause both the appropriate concentrate 18 and the water 10 to be dispensed in appropriate quantities into the mixing chamber 16 and hence to the dispensing outlet 2.

The mixing chamber 16 may be of any suitable construction. In this respect, appropriate mixing chambers for receiving and mixing different liquids are available currently and may be utilized in the system of FIG. 1. As the construction of the mixing chamber 16 is not part of this invention, it is not further described herein.

Because the rate at which the liquids are dispensed is controlled by the valves 14 in dependence upon the rates of flow in the tubing 12 and 20, the control of the liquid dispensed is very reliable and reliable mixing of two liquids in selected proportions can be achieved. Furthermore, much more sophisticated control is also possible, as the system can be arranged to provide flexibility to choose the quantity of liquid to be dispensed and the rate at which the liquid is dispensed. In this respect, it is useful to be able to control the flow rate depending upon the amount of liquid to be dispensed. Thus, if only a small portion is to be dispensed, it is normally required that this be done slowly. However, where larger quantities are to be dispensed, for example, to fill a pint of liquid, such quantities need to be dispensed quickly. Even if a large quantity is to be dispensed quickly, it is also advantageous for the flow rate to be profiled so that there is a slow initial rate which is subsequently considerably increased. This reduces the risk of splashing. To achieve such control, it is possible to provide on the keypad keys 30 by which the quantity is determined so that the dispense is totally under the control of the processor 6. Alternatively, the operator may be allowed to control the dispensing by keeping the appropriate key 30 depressed. In this case, the processor 6 may control the flow to begin slowly, so that a small portion is dispensed slowly. However, if more than a first quantity is dispensed, the processor 6 may then increase the flow rate considerably. The keypad 8 has a number of LEDs 32 associated with each key 30. Each LED 32 is preferably illuminated when a particular key 30 is, or has been depressed, to indicate the dispensing operation which is being undertaken.

It has been stated above that the system as shown in FIG. 1 may be used to control or prevent fraudulent substitution of imitation liquids. It is not unknown, for example, for the manager of a public house or café to buy cheaper imitation colas, rather than the branded versions, or to dilute the branded versions with water. However, such imitation colas have physical characteristics which differ from those of the proprietary brands, and the processor 6 may be arranged to recognise and/or respond to such differences.

The flow rate readings provided by each flow transducer 22 may be the times taken by the ultrasonic pulses to travel through the liquid flowing therein between two ultrasound transmitting/receiving faces of the transducer. The software of the processor 6 can use this time data to determine the liquid flow rate. If the processor 6 is also provided with the accurate length of the distance between the two transmitting/receiving faces it will also be able to accurately determine the speed of sound in the liquid in the transducer.

The speed of sound in a liquid varies with temperature, and a graph of sound speed against temperature can be obtained, and stored in the processor 6, for each proprietary branded liquid the system is set up to dispense. Each flow transducer 22 is also provided with temperature sensing means, such as a thermistor 65, arranged to provide temperature measurements which are, or substantially are, the temperature of the liquid flowing in the transducer 22. The processor 6 is arranged to compare the determined speed of sound in the liquid at the measured temperature with the stored expected value at that temperature. If the determined speed is not the same as the stored expected value within predetermined tolerances the processor 6 is arranged to provide a signal that the liquid is a substitution. In this respect, the processor 6 may store a range of acceptable speed values for the proprietary brand at each temperature, and/or may store tolerance limits. Generally, a liquid will be identified as a substitute or fraud if the determined speed is not within 3 standard deviations of the stored, expected value.

When the processor 6 detects an imitation, such as an imitation cola, it may be arranged to close down the system, for example by shutting off all of the proportional valves 14. Not only would this require the system manager to seek assistance to restart the system, but the detected imitation cola will remain trapped within the tubing 20, for example, enabling it to be retrieved for analysis. This fraud detection application of the system is particularly useful where the hand held terminal 5 is provided, as the terminal can be linked to the processor 6 to reset the system in a simple and accurate manner.

Figure 2:
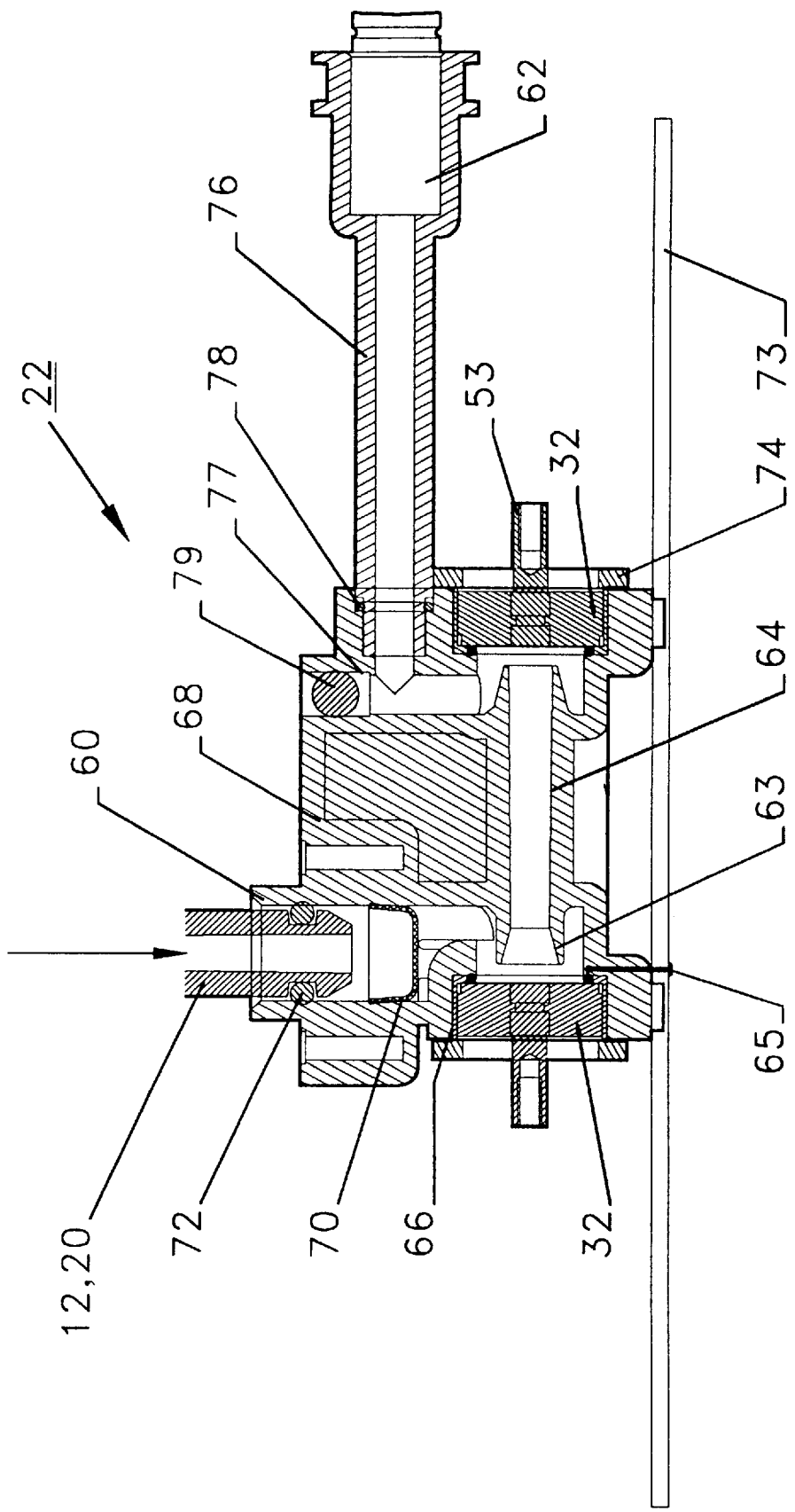
FIG. 2 shows a section through an embodiment of a flow transducer for determining the flow rate of a fluid.

FIG. 2 shows a section through one embodiment of a flow transducer 22. As indicated in FIG. 1, the liquid in the tubing, as 12 or 20, is arranged to flow through a respective flow transducer 22. As the liquid flows through the transducer it is subjected to ultrasonic pulses applied thereto by two sensors 32. A section through a sensor 32 is shown in FIG. 3.

Figure 3:
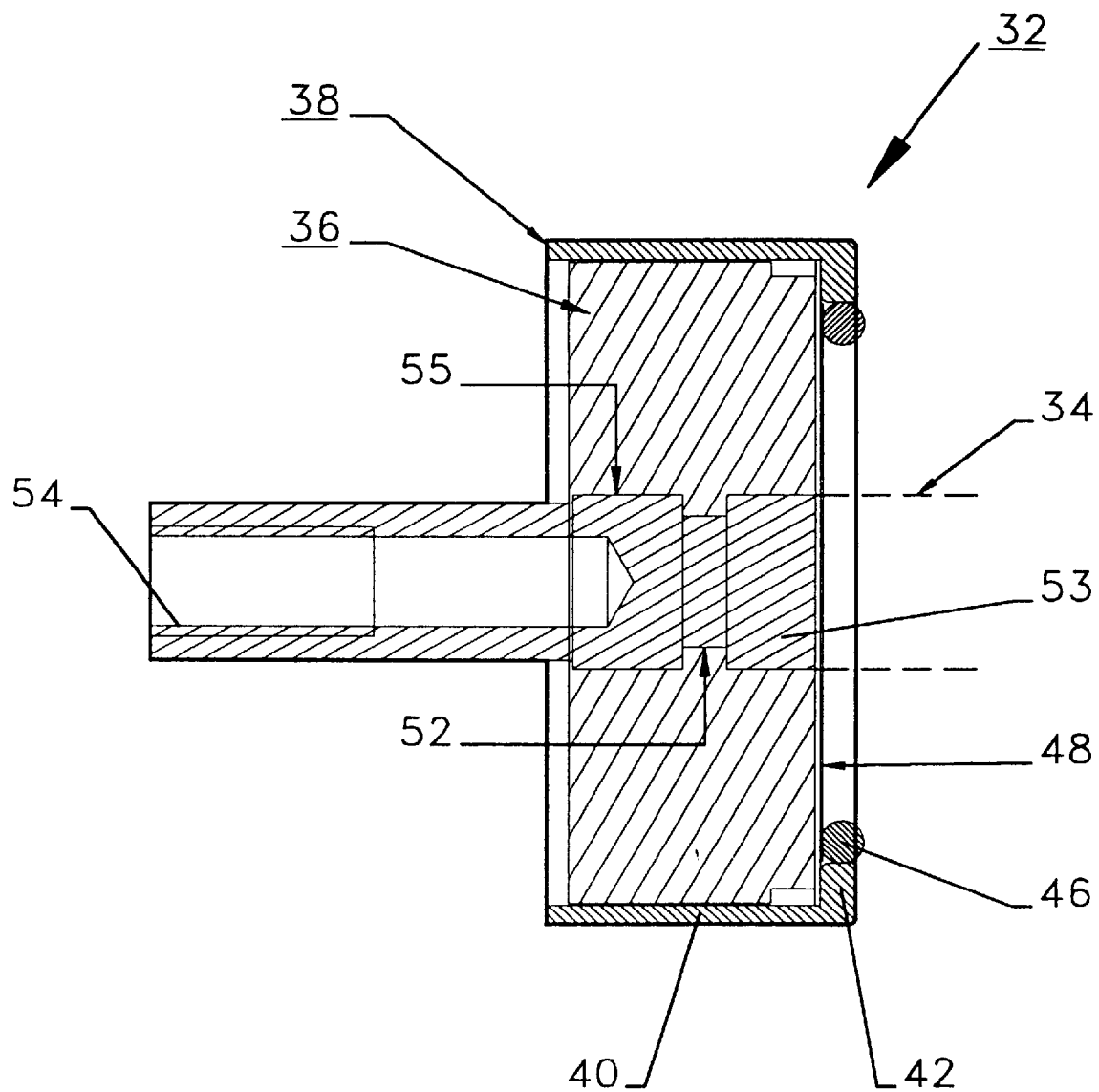
FIG. 3 shows a section through a sensor of the transducer of FIG. 2.

The sensor 32 illustrated in FIG. 3 is a piezoelectric device which can be energized to output an ultrasonic waveform, indicated schematically at 34, from a central area thereof. The sensor 32 comprises a substantially cylindrical body 36 of plastics material. This body 36 is received within a substantially cylindrical housing 38. In the embodiment illustrated, the housing 38 has a substantially cylindrical peripheral wall 40 which is made of metal and which has at its front end an annular, radially inwardly extending flange 42 which is similarly made of metal. The body 36 is retained in position within the cylindrical housing 38 by way of crimps or indentations (not shown) formed in the wall 40 to bite into the body 36. The front radially extending flange 42 defines a circular opening in the housing 40 across which a piezoelectric element 48 extends.

The piezoelectric element 48 comprises a circular thin film of PVDF having a film of gold deposited over substantially all of its front surface. The ultrasonic waveform 34 is generated by applying an electrical potential across the thickness of the piezoelectric element 48 by way of a metal contact post 53. This contact post 53 is provided with a flat, substantially circular contact surface which is held in abutment with the rear surface of the piezoelectric element 48. Thus, the circular contact surface of the post 53 opposes and overlies a corresponding area of the gold film on the front surface of the element 48 and it is these aligned conductive areas which apply the electrical potential across the element 48 and thereby define a circular area of the sensor 32 from which the ultrasonic waveform 34 is emitted. In this respect, in the circular, substantially central area of the element 48, where the gold film is aligned with the contact surface of the contact post 53, mechanical vibrations caused by the piezoelectric effect generate the ultrasonic waveform. With the present invention, the waveform generated is a series of ultrasonic pulses.

The necessary electrical connections are made to the front surface of the piezoelectric element 48 by way of the housing 38. In this respect, it will be appreciated that the radial flange 42 surrounds and is in contact with the circumference of the gold covered front surface of the element 48. Preferably, a conductive paste, not visible, is inserted along the area of contact between the flange 42 and the gold covered surface to enhance the connection. The electrical connection to the housing 38 is made by way of a metal clamp 74 which is shown in FIG. 2.

The sensor 32 shown in FIG. 3 is extremely simple to make. The contact post 53 is a generally cylindrical post having a reduced diameter portion 52 defining a key portion for retaining the post 53 with the body 36. At its end projecting rearwardly of the cylindrical body 36, the contact post 53 is tapped to form a cylindrical longitudinally extending bore 54 which is internally screw threaded, at least at its outer end. The contact post 53 is also knurled on a part 55 of its outer surface.

The contact post 53 is moulded into the cylindrical body 36. Thus, the post 53 is positioned in a mould for the body 36 and then the plastics material is formed therearound. The reduced diameter portion 52 acts to key the post 53 in position, and this key portion and the knurling on the outer surface part 55 of the post 53 prevent axial movement and rotation of the post 53 relative to the plastics material body 36. After moulding, the front surface of the combined body 36 and post 53 is machined flat. This is necessary to ensure that the piezoelectric element 48 when adhered to the front surface is reliably in contact with contact surface of the post 53. It will be appreciated that the post 53 forms the electrode for the sensor 32, and an electrical terminal (not shown) can be connected thereto by screwing it into the bore 54.

Once the plastics material body 36 and post 53 have been assembled, the piezoelectric element 48, to the front surface of which the gold film has been bonded, is adhered to the machined front surface of the assembly. The resultant assembly is then inserted into the cylindrical housing 38 so that the gold film of the element 48 is in electrical contact with the flange 42. The assembly of the sensor 32 is completed by crimping or otherwise indenting the peripheral wall 40 of the housing 38 to hold the assembly together.

The contact post 53 is made of a metal which is particularly rigid and acts, when electrical potential is applied across the element 48, to provide a high acoustic impedance so that the ultrasonic pulse is sent into the liquid. Preferably, the post 53 is made of stainless steel As will be apparent from FIG. 2, the liquids whose flow rate is to be measured by the transducer 22 will come into contact with the front surface of the piezoelectric element 48 of the sensor 32. For this reason, the electrically conductive film used on the front surface of the element 48 is preferably gold as this is inert. However, it is also preferred that a film of a food approved barrier material (not shown) is bonded to the front surface of the element 48. Furthermore, and as is shown in FIG. 3, an O ring 46 is mounted in the opening defined by the flange 42 to seal the sensor 32 against the ingress of liquid.

The simple construction of the sensor 32 illustrated in FIG. 3 lends itself to mass production. The construction is very much simpler than prior art sensors, for example used in scientific apparatus, but is has been found that its performance is more than adequate for a system of the invention.

Two of the sensors 32, as described above, and as illustrated in FIG. 3, are incorporated in the flow transducer 22 which is illustrated in FIG. 2. As can be seen, the flow transducer 22, which is preferably fabricated of a plastics material, comprises a liquid inlet 60 to which tubing, as 12,20, is connected, and a liquid outlet 62 which is similarly connected to the tubing, as 12,20. Thus, it will be appreciated that liquid in the tubing enters the transducer 22 through the inlet 60, flows through the transducer, and subsequently flows out of the transducer by way of the outlet 62. Between the inlet 60 and the outlet 62 the transducer is provided with a measuring bore or chamber 64 through which the liquid has to flow. In the illustrated embodiment, the measuring bore 64 is a longitudinally extending bore of circular cross-section which, at each of its ends, faces the front of a respective sensor 32. The centre line of the bore 64 is aligned with the centre of the central emitting area of each sensor 32. This means that sound beams emitted by each sensor 32 are aligned with, and travel along, the central longitudinal axis of the measuring bore 64.

Preferably, the transducer 22 has a housing 68 which is moulded in one piece from a suitable plastics material, such as acetal. As a liquid is to be flowed through the transducer 22 it is advantageous that the housing 68 is made from only a single moulding. The provision of a single moulding means that there are no interconnected parts and thus that there are no sealing problems associated therewith.

As described above, the housing 68 defines a measuring bore 64. Furthermore, two opposed cylindrical recesses 66 are defined in the housing 68 in each of which a respective sensor 32 is received. The arrangement is such that each sensor 32 can be mounted so that the front, beam emitting surface thereof, defined by the front surface of the piezoelectric element 48, is spaced from the adjacent end of the measuring bore 64. The emitting surfaces of the sensors 32 form the transmitting/receiving faces of the transducer 22 referred to above.

In the illustrated embodiment, the thermistor 65 for measuring the temperature of the liquid in the measuring bore 64 extends within a narrow bore moulded in the housing 68. The temperature sensitive head of the thermistor 65 is arranged to be separated from the measuring bore 64 by only a very thin layer of the plastics material and is inserted in silicone grease. The thermistor 65 is thus in good thermal contact with the liquid in the measuring bore 64.

The liquid inlet 60 has a longitudinal axis which extends substantially perpendicularly to the centre line of the measuring bore 64 whereas the axis of the outlet 62 is substantially parallel to the centre line of the measuring bore 64 but laterally offset relative thereto. This arrangement forces liquid flowing into the transducer 22 to take a tortuous path into the measuring bore 64, this path causing the liquid to flow symmetrically across the front surface of the sensor 32 at the upstream end of the bore 64. Similarly, liquid leaving the measuring bore 64 follows a tortuous path to the outlet 62, and again this tortuous path takes the liquid across the front surface of the downstream sensor. This tortuous path is important in providing the required type of liquid flow through the measuring bore 64, as described below.

It will be seen that there is provided in the liquid inlet 60 a gauze filter 70 to remove any contaminants from the liquid. It will also be seen that in the embodiment of FIG. 2 the tubing 12, 20 is provided with an appropriate shaped end for insertion into the inlet 60, that end carrying an appropriate O ring seal 72. The tubing 12, 20 may be a push fit in the inlet 60 and/or secured therein by any suitable means (not shown).

The outlet 62 is defined by an extension pipe 76 which, in this embodiment, is moulded separately from the housing 68 and affixed thereto by any suitable means. A respective O ring 78 ensures that the joint between the pipe 76 and the housing 68 is appropriately sealed. In moulding the relatively complex shape of the housing 68 it may be necessary to have a bore, as 77, accommodating a moulding core. This is simply sealed by pressing a glass ball 79 therein.

The geometry of the housing part 68 of the transducer 22, and particularly of the flow paths for the liquid is important in providing the appropriate flow along the measuring bore 64. It would be possible to arrange that the liquid flow along the measuring bore 64 is substantially laminar. However, and as is well known, different parts of a flow travel at different velocities and with laminar flow the difference in velocity between that at the centre line and that at the periphery of the bore 64 is very marked. More importantly, the nature of the liquid flow along the measuring bore 64 will change as the liquid moves along the bore and approaches the laminar profile, and this causes changes in the centre line velocity. It is preferred that the flow along the measuring bore 64 have a fairly uniform centre line velocity.

The flow which is achieved is the result of the geometry of the flow path and it will be seen that at its inlet the measuring bore 64 has an inwardly tapering section 63. This tapering section 63 is shaped so that it does not introduce turbulence into the liquid as it enters the bore 64. For the same reason, the external rim of the tapering section 63 has a gently curved profile and is not truncated. This rim profile shape also acts to avoid the introduction of turbulence into the liquid entering the measuring bore 64.

The tapering section 63 leads into the measuring bore 64 which is longitudinally extending and circular in cross-section. However, the bore 64 does not have a constant cross-sectional size along its length. Instead, the bore 64 tapers outwardly along the direction of flow, that is, it diverges towards its outlet end. It has been found that this gentle taper holds the flow and ensures that it has a fairly uniform centre line velocity. The taper must be gentle, and it is preferred that it does not exceed a 2° included angle. Preferably, the included angle will be in the range of 0.5° to 1°, and it has been found that an included angle of 0.67° is particularly effective.

The ultrasonic beam 34 generated by each sensor 32 is confined in width, and for example, is of the order of 4 mm in diameter. Each beam 34 is aligned with the central axis of the measuring bore 64. This ensures that the flow rate measured by the transducer 22 will be substantially the centre line velocity, which, as we have seen, is arranged to be substantially constant. Thus, the effect of any friction at the periphery of the bore 64 is ignored.

It is important to hold the flow in a substantially known shape and to avoid the introduction of turbulence into the flow as this makes it possible mathematically to compute the flow. Such computation is necessary in order to provide the appropriate information about flow rates to the processor 6.

The method by which the transducer 22 enables the flow rate of the liquid through the bore 64 to be measured is generally known and will not be described in great detail. Briefly, an electrical pulse is applied to the upstream sensor 32 such that an ultrasonic pulse is emitted thereby and travels along the bore 64 with the liquid flow. The time taken by the ultrasound pulse to reach and be sensed by the downstream sensor 32 is measured. An electrical pulse is then applied to the downstream sensor such that, in its turn, it emits an ultrasound pulse which travels upstream in the bore 64 against the flow. Again, the time between firing of the pulse and it being received by the upstream sensor is measured. It will be appreciated that from the two time measurements made, the speed of the flow of the liquid within the measuring bore 64 can be determined.

In the embodiment illustrated, a printed circuit board 73 is carried by the housing 68 of the transducer and is arranged to control the application of electrical pulses to the sensors 32 and to detect the receipt of ultrasonic pulses. The thermistor 65 is also connected to the printed circuit board 73 so that temperature measurements can be supplied to the processor 6. It will be seen that the housing 68 and the printed circuit board 73 are interengaged. It will also be appreciated that the metal clamp 74 at each end of the transducer 22, to contact the sensor housings, and the contact post 53 can be electrically connected to the printed circuit board 73 to receive power therefrom. For example, a wire (not shown) connected to the circuit board 73 can be electrically connected to the clamp 74 by way of a screw also used to hold the metal clamp 74 in position relative to the housing 68. Thus, the metal clamp 74 not only holds a respective sensor 32 in position, but also makes the necessary electrical connection therewith. The printed circuit board 73 may carry the transducer circuit 28 (FIG. 1) which is arranged to control the firing of ultrasonic pulses. The circuit board 73 will also be connected, for example, by way of the transducer circuit 28, to the processor 6. By this means, the time taken for ultrasonic pulses travelling upstream and downstream within the measuring bore 64 can be fed to the processor 6 which is thereby enabled to compute the flow rate of liquid through the bore 64. The information and the computations made therefrom are used to control the dispensing of liquid by way of the proportional valves 14.

The software within the processor 6 enabling the computations to be made is within the competence of any one skilled in the art and is not further described herein. However, it is important to note that in order to obtain a fully responsive dispensing system, it is necessary for the flow rate to be determined regularly, for example fifty times a second.

In the embodiment illustrated, housing 68 of the transducer 22 is formed in one piece. Of course, it is possible for the housing to be made in more than one piece with the individual parts appropriately held together. With such a construction, parts of the transducer where liquid flow is not required are sealed by way of appropriate O rings.

The processor 6 is, as we have seen, able to determine the rate of flow of any liquid as 10,18 in its tubing 12,20. In response to the flow rate determined, and in response to the instructions received from the keypad 8, the processor 6 actuates an appropriate proportional valve 14 to dispense the liquid to a dispensing outlet 2 or 4. In this respect, to ensure that the system is fully responsive, the proportional valves 14 are constructed to change the rate at which liquid is dispensed in fractions of a second.

Figure 4:
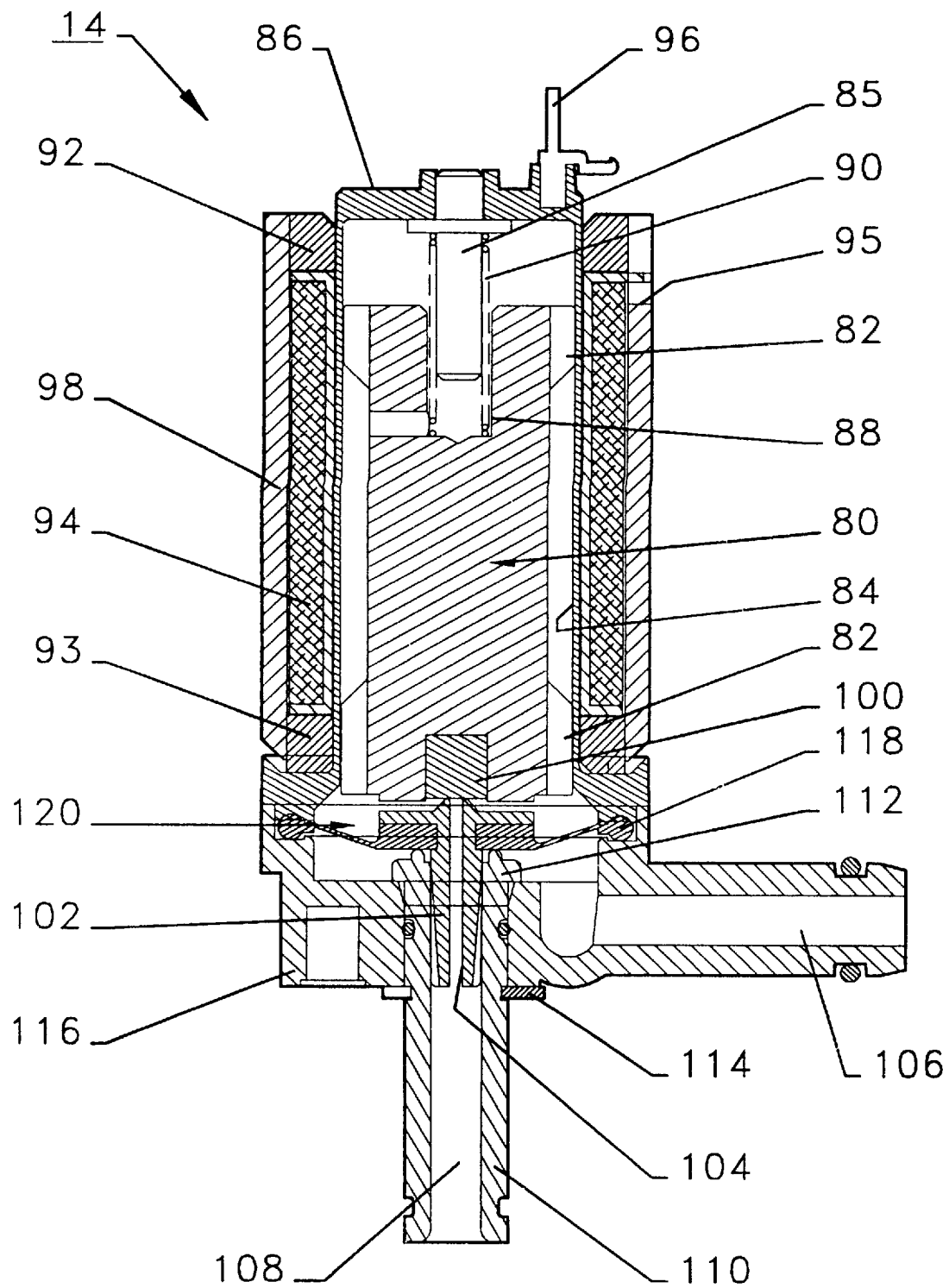
FIG. 4 shows a longitudinal section through an embodiment of a proportional valve for controlling the flow of a fluid.

A longitudinal section through one embodiment of a proportional valve 14 is shown in FIG. 4. This valve 14 includes a movable magnetic armature 80 and it is the position of this armature which, as will be clear from the description below, determines the rate of flow of liquid therethrough. The armature 80 is preferably made of magnetic stainless steel and is in the form of a dumb-bell having radially extending pole pieces 82 at each end thereof. The armature 80 is slidably mounted within a generally cylindrical housing 84 having a base 86. At its end nearest to the base 86, the armature 80 has a longitudinally extending bore 88 in which a spring 90 is mounted. The spring 90 acts to bias the armature 80 away from the base 86. Preferably, and as illustrated, the housing 84 is formed to have a central post 85 extending away from the base 86 substantially axially to locate and guide the spring 90 and to act as a stop for the upward movement of the armature 80.

Two annular pole pieces 92 and 93 are mounted to extend around the housing 84 and are separated by a coil 94 which is connected by way of leads 96 to receive electrical power under the control of the processor 6. A cylindrical sleeve 98 of mild steel is positioned around the pole pieces 92, 93 and the coil 94 to provide a return path for the magnetic circuit. The leads 96 extend through a recess 95 provided in the sleeve 98.

In the position of the armature 80 shown in FIG. 4, which is the position thereof determined by the spring 90, it will be seen that the upper pole piece 82 of the armature is displaced from the corresponding upper pole piece 92. The lower pole pieces 82 and 93 remain overlapped to feed magnetic flux into the magnetic circuit. It will be appreciated that if current is fed to the coil 94 at a sufficient amplitude to overcome the force of the spring 90, the magnetic field generated thereby and appearing in the upper pole pieces 92 will be sufficient to attract the corresponding upper pole piece 82 of the armature. Furthermore, once the initial bias has been overcome, increasing the current and hence the magnetic field, increases the attractive forces. It can be shown that the amount of movement of the armature pole piece 82 towards the pole piece 92 is directly proportional to the amplitude of the applied current. Of course, once the pole pieces 82 and 92 are aligned, no further movement of the armature 80 will take place. However, the armature 80 will generally have come into abutment with the stop 85 before this happens.

Of course, it will also be appreciated that the armature 80 cannot simply be used to control the opening of a valve member to provide a proportional flow of a fluid. In this respect, as soon as the armature 80 moves sufficiently to allow a valve member to open slightly, the pressure force of the fluid on the armature 80 drops and acts to further open the valve member and to move the armature irrespective of the amplitude of the current applied thereto. To overcome this problem, the valve 14 shown in FIG. 4 provides for that liquid to be controlled and to be applied to the valve member both in a direction to open the valve and in an opposing direction. As the liquid forces are thereby balanced, the opening of the valve can be determined solely by the electrical supply applied to the magnetic circuit. Furthermore, in a valve of the invention, the valve member is shaped that the further it moves away from its closed position the greater is the area of the flow path for liquid. Thus, the flow rate of liquid through a valve of the invention, at a given pressure, is substantially directly proportional to the amplitude of the electrical current supplied.

As shown in FIG. 4, the armature 80 has a pad 100 received within a corresponding bore formed in its projecting end. The surface of the pad 100 defines a valve seat and, in the closed position of the valve, the valve seat engages an end of a main valve member 102 in which a pilot tube 104 opens. In this respect, it will be seen that the pilot tube 104 extends through the main valve member 102. The main valve member 102 controls the communication between a liquid inlet port 106 and a liquid outlet port 108. The outlet port 108 is provided at one end of a tubular member 110 at whose other end the main valve seat 112 is defined. It will be seen that a longitudinal bore extends through the tubular member 110. An external annular groove is provided in the tubular member 110 and receives a securing disk or circlip 114. The securing disk 114 together with an outwardly extending flange provided on and surrounding the main valve seat 112 securely fastens the tubular member 110 on a valve body 116 in which the inlet port 106 extends.

Between the open end of the housing 84 and the valve part 116 a diaphragm 118 is secured. This diaphragm 118, which is also received in an annular groove of the main valve member 102, defines a pilot chamber 120. A small hole (not visible) extends through the diaphragm 118 such that liquid at the inlet port 106 of the valve enters and fills the pilot chamber 120.

In the closed position of the valve 14, which is shown in FIG. 4, liquid under pressure at the inlet 106 passes through the hole in the diaphragm 118 into the pilot chamber 120 and therefore acts on both surfaces of the diaphragm 118. In this position, the spring 90 and the pressure acting on the main valve seat 112 keeps the valve closed. If an electric current is then applied to the coil 94 and is sufficient to overcome the force of the spring 90 and all of the other small forces acting to keep the pilot valve closed, the magnetic forces will move the armature 80 against the action of the spring and other forces in a direction to open the valve. In this respect, it will be appreciated that as well as the force of the spring 90, there will be liquid pressure acting to keep the pilot valve closed as well as forces of gravity and friction and the like. The opening movement, of course, is upwardly, as is shown in FIG. 4.

As the armature 80 begins to lift, the valve pad 100 carried thereby is lifted from the end of the pilot tube 104 and liquid in the pilot chamber 120 flows through the tube 104 in the main valve member 102 and to the outlet port 108. This flow reduces the pressure in the pilot chamber 120 as compared to the pressure on the other side of the diaphragm 118, and hence the diaphragm 118 begins to lift away from the main valve seat 112 and in doing so lifts the main valve member 102. Flow of liquid from the inlet port 106 to the outlet port 108 through the main valve seat 112 therefore commences. However, the pilot chamber 120 remains in communication with the liquid inlet 106 via the small hole in the diaphragm 118. As the upwardly moving main valve member 102 approaches pad 100 the flow into the pilot tube 104 is reduced. Automatically a balance point is established where all forces acting on either side of the diaphragm 118 are equal so that it remains stationary at the position dictated by the pad 100 carried by the armature 80. Movement of the armature 80 therefore continues to a position which is determined by the amplitude of the electrical current applied to the coil 94. As the armature 80 moves upwardly, it causes the valve member 102 to move upwardly in the same manner by a repetition of the process described above on initial opening. Thus, it will be appreciated that the valve member 102 moves upwardly by a distance which is substantially equal to the movement which has been undertaken by the armature 80.

The valve member 102 has a converging cross-section and thus as it lifts out of the tubular member 110 the area of the flow path it defines with the bore 108 thereof increases. It will thus be seen that the valve shown in FIG. 4 acts substantially as an accurate proportional valve. Thus, the amplitude of the current applied to the coil 94 determines the position of the armature 80 and hence of the valve member 102. The further the valve member 102 is removed from the tubular member 110 the greater is the area of the flow path. Thus, the flow at a given pressure allowed by the valve is substantially directly proportional to the amplitude of the current supplied. This can, of course, be used to ensure that the liquid dispensed by the system of FIG. 1 is always reliably determined by the electrical control signals applied thereto by the processor 6.

Of course, the amplitude of the current supplied to the coil 94 can be changed substantially instantaneously under the control of the processor 6 to respond to demands for high or lower rates of flow or for increased or decreased liquid quantities. The flow dispensed by the proportional valve 14 of FIG. 4 can similarly be changed in a fraction of a second in response to a change in the current amplitude.

For any given pressure, it is the position of the valve member 102 relative to the bore 108 which determines the flow through the valve 14. Of course, the flow rate will depend upon the pressure of the liquid, but the valve 14 is controllable to provide exactly the quantity of liquid required irrespective of the pressure of the liquid flowing into the inlet 106. Thus, if the pressure of the incoming liquid falls, so that the flow rate in the tubing also falls, an increase in the current amplitude applied to the coil 94 will open the valve 14 further to increase the flow rate therethrough. Of course, it will be appreciated that the flow rate through the valve 14, and hence through the tubing connected thereto, is detected by an appropriate transducer 22.

The amount of taper of the tapering external surface of the valve member 102 can be chosen as required. This tapering external surface also carries a plurality of longitudinally extending vanes (not shown) which project radially and increase in their radial extent as the radius of the external profile of the valve member 102 decreases. This means that the longitudinally extending surfaces of the vanes contact the interior surface of the bore 108 along their entire length. The vanes therefore ensure that the valve member 102 is constrained to move substantially lineally along the longitudinal extent of the bore 108 and the vanes prevent any twisting movement of the valve member 102.

In the above description, the flow transducer, the sensor, and the proportional valve have all been described in conjunction with a dispensing system for beverages. Of course, each of these components may be used alone or in alternative systems and none of these components is limited in application to the system of the invention.

It will be appreciated that particular components of the system, and the system as described and illustrated, are provided by way of example only and various modifications and variations may be made thereto within the scope of this application.

I claim:

1. A piezoelectric sensor for a sonic transducer, said sensor comprising a housing defining an opening, a plastics material body within said housing, a piezoelectric element comprising a piezoelectric film supported to extend across said opening, said piezoelectric film having a first, inner surface, and an opposed, second, outer surface, first and second electrically conductive regions, the first electrically conductive region contacting said first surface of said piezoelectric film, the second electrically conductive region contacting said second surface of the piezoelectric film, and said first and second electrically conductive regions overlying to define one area of said piezoelectric film at which said first and second conductive regions coincide, and means for making electrical connections to said conductive regions, wherein said means for making electrical connections comprises an electrically conductive post extending through said plastics material body, said post having an end surface contacting said first, inner surface of said piezoelectric film at said one area thereof, said plastics material body having a front surface which together with said end surface of said conductive post defines a combined support surface for said piezoelectric film, and wherein said means for making electrical connections to said conductive regions further comprises a radially extending flange having an inner surface and defining the opening of said housing, said inner surface of said flange contacting a periphery of the second, outer surface of said piezoelectric film.

2. A piezoelectric sensor according to claim 1, wherein said combined support surface is flat and supports the full extent of the piezoelectric film, and wherein said conductive post extends substantially transversely with respect to said piezoelectric film.

3. A piezoelectric sensor according to claim 1 or claim 2, further comprising conductive paste inserted along the area of contact between said inner surface of the flange and the outer surface of the piezoelectric film.

4. A piezoelectric sensor according to claim 1, wherein said end surface of the conductive post, which is in contact with said first surface of said piezoelectric film, defines one of said electrical conductive regions, and wherein an electrically conductive film is provided on the said second, outer surface of said piezoelectric film to define the other one of said electrically conductive regions.

5. A piezoelectric sensor according to claim 4, wherein the electrically conductive film is a film of gold.

6. A piezoelectric sensor according to claim 1 or claim 4, wherein the piezoelectric film is a film of polyvinylidene flouride (PVDF).

7. A piezoelectric sensor according to claim 1 or claim 4, wherein the piezoelectric film is generally circular, and wherein said one area of the piezoelectric film is substantially circular and is located substantially centrally of the piezoelectric film.

8. A piezoelectric sensor according to claim 1, wherein said plastics material body is substantially cylindrical and has an axial bore therethrough in which said conductive post extends, said bore extending substantially centrally of the plastics body.

9. A piezoelectric sensor according to claim 8, wherein said plastics material body has been moulded around said conductive post.

10. A flow transducer for measuring the flow rate of a fluid, said flow transducer comprising an elongate, substantially linear measuring chamber having an upstream end and a downstream end, and along which a fluid is arranged to flow from the upstream end to the downstream end, an upstream sensor at said upstream end of said measuring chamber, and a downstream sensor at said downstream end of said measuring chamber, wherein said sensor is controllable to emit and/or receive a sound beam and is arranged such that sound beams emitted pass along said measuring chamber, wherein said measuring chamber is arranged to diverge in the direction of fluid flow, and wherein each said sensor comprises a housing defining an opening, a plastics material body within said housing, a piezoelectric element comprising a piezoelectric film supported to extend across said opening, said piezoelectric film supported to extend across said opening, said piezoelectric film having a first, inner surface, and an opposed, second, outer surface, first and second electrically conductive regions, the first electrically conductive region contacting said first surface of said piezoelectric film, the second electrically conductive region contacting said second surface of the piezoelectric film, and said first and second electrically conductive regions overlying to define one area of said piezoelectric film at which said first and second conducive regions coincide, and means for making electrical connections to said conductive regions, wherein said means for making electrical connections comprises an electrically conductive post extending through said plastics material body, said post having an end surface contacting said first, inner surface of said piezoelectric film at said one area thereof, said plastics material body having a front surface which together with said end surface of said conductive post defines a combined support surface for said piezoelectric film, and wherein said means for making electrical connections to said conductive regions further comprises a radially extending flange having an inner surface an defining the opening of said housing, said inner surface of said flange contacting a periphery of the second, outer surface of said piezoelectric film.

11. A flow transducer according to claim 10, wherein the diverging measuring chamber includes an angle which does not exceed 2°, and is preferably in the range 0.5° to 1°.

12. A flow transducer according to claim 10, wherein a section of said measuring chamber at the upstream end thereof is tapered inwardly in the direction of fluid flow.

13. A flow transducer according to claim 10, further comprising a fluid inlet communicating with the measuring chamber to supply fluid thereof, and a fluid outlet communicating with the measuring chamber to receive fluid therefrom, wherein each of the upstream and downstream sensors has a respective transmitting face, and wherein a tortuous patch for the fluid is defined between the fluid inlet and the measuring chamber, and between the measuring chamber and the fluid outlet, the arrangement being such that fluid is constrained to flow substantially symmetrically across said transmitting face of both the upstream and the downstream sensors.

\* \* \* \* \*